(12) United States Patent
Frolov et al.

(10) Patent No.: US 8,394,620 B2
(45) Date of Patent: Mar. 12, 2013

(54) TWO-COMPONENT GENOME FLAVIVIRUS AND USES THEREOF

(75) Inventors: Ilya V. Frolov, Galveston, TX (US); Alexandr V. Shustov, Astana (KZ)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 12/151,491

(22) Filed: May 7, 2008

(65) Prior Publication Data

US 2009/0324623 A1    Dec. 31, 2009

Related U.S. Application Data

(60) Provisional application No. 60/927,993, filed on May 7, 2007.

(51) Int. Cl.
*C12N 7/00* (2006.01)
*A61K 39/12* (2006.01)

(52) U.S. Cl. .................. 435/235.1; 424/218.1; 435/69.1

(58) Field of Classification Search ........................ None
See application file for complete search history.

(56) References Cited

U.S. PATENT DOCUMENTS

| | | | |
|---|---|---|---|
| 6,497,884 B1 | 12/2002 | Plentiv et al. | |
| 6,569,435 B1 | 5/2003 | Punnonen et al. | |
| 6,676,936 B1 | 1/2004 | Lai et al. | |
| 6,943,015 B2 * | 9/2005 | Frolov et al. | ............... 435/320.1 |
| 7,094,411 B2 | 8/2006 | Kinney et al. | |

OTHER PUBLICATIONS

Mason et al. Virology, 2006, 351:432-443.*
Shustov, Alexander V., et al., "Production of Pseudoinfectious Yellow Fever Virus with a Two-Component Genome", Journal of Virology, Aug. 2007, 11737-11748, 81(21), American Society for Microbiology.

* cited by examiner

*Primary Examiner* — Stacy B. Chen

(57) ABSTRACT

The present invention discloses a two-component genome flavivirus and a method for propagating such virus. Since the genetic material of this flavivirus is distributed between two genomes, the flavivirus is deficient in replication, incapable of causing disease but capable of inducing an immune response. Nevertheless, the design of the replication deficient flavivirus discussed herein allows propagation of these flaviviruses at industrial level.

14 Claims, 7 Drawing Sheets

TWO-COMPONENT GENOME FLAVIVIRUS AND USES THEREOF

CROSS REFERENCE TO RELATED APPLICATION

This non-provisional application claims benefit of provisional application U.S. Ser. No. 60/927,993 filed on May 7, 2007, now abandoned.

FEDERAL FUNDING LEGEND

This invention was produced in part using funds obtained through National Institute of Health grant (5 U54AI057156). Consequently, the federal government has certain rights in this invention.

BACKGROUND OF THE INVENTION

1. Field of the Invention

The present invention relates to the fields of molecular biology, virology and immunology. More specifically, the present invention provides replication deficient flaviviruses and discloses its use as vaccine against flavivirus-associated diseases.

2. Description of the Related Art

The Flavivirus genus of the Flaviviridae family contains a variety of important human and animal pathogens that include yellow fever, tick-borne encephalitis, Japanese encephalitis, dengue, West Nile, classical swine fever, bovine viral diarrhea and hepatitis C viruses. In nature, flaviviruses circulate between vertebrate hosts and arthropod vectors mainly represented by a large number of mosquito and tick species. Almost fourty members of this genus, classified into four distinct antigenic complexes, are capable of causing human disease.

The flavivirus genome is a single-stranded RNA of positive polarity of almost 12 kb. It encodes a single polypeptide that is co- and post-translationally processed by cellular and viral proteases into viral structural proteins, C, prM/M, and E, that form infectious viral particles, and the nonstructural proteins, NS1, NS2A, NS2B, NS3, NS4A, NS4B and NS5, that form the enzyme complex required for replication of viral genome (Lindenbach and Rice, 2001). The flavivirus genome mimics the structure of cellular messenger RNAs by having a 5' methylguanylate cap, but differs from the cellular RNA templates by the absence of a 3'-terminal poly(A) sequence.

In flavivirus virions, a single copy of viral genomic RNA is packaged by the C (capsid) protein into nucleocapsid surrounded by lipid envelope with embedded dimers of E and the M protein. The mechanism of interaction between the nucleocapsid and the envelope is not completely understood yet, but it appears to be less specific than, for instance, the alphavirus nucleocapsid-envelope interaction, and the flavivirus virions can be efficiently formed by capsid and envelope proteins derived from the viruses that belong to distant antigenic complexes (Chambers et al., 1999; Lorenz et al., 2002; Monath et al., 2002). Moreover, the presence of nucleocapsid is not an absolute requirement for particles assembly, and virus-like particles formation and release from the cells can be achieved by expression of only prM and E from a wide variety of vectors. These so-called subviral particles (SVPs) contain no RNA or capsid protein (Mason et al., 1991), but have the envelope proteins organized into icosahedral, lipid-containing structure. The prM/E-embedded subviral particles are capable of inducing an efficient immune response that protects animals against following infection with the replication-competent viruses (Konishi and Fujii, 2002; Konishi, Fujii, and Mason, 2001; Konishi et al., 1992; Qiao et al., 2004), DNA (Aberle et al., 1999; Colombage et al., 1998; Davis et al., 2001; Kochel et al., 1997; Kochel et al., 2000; Konishi et al., 2000a; Konishi et al., 2000b; Phillpotts, Venugopal, and Brooks, 1996; Schmaljohn et al., 1997). The lack of nucleocapsid-packaged replication-competent RNA makes application of subviral particles as potential vaccines very advantageous, but requires development of new means for their large-scale production or delivery of the expression constructs. The prM/E-expressing cassettes can be designed on the basis of viral and nonviral vectors. In the case of viral vectors, there is always a concern of either the development or pre-existence of the immune response to the used viral vector. The DNA-based cassettes, encoding these genes under control of efficient RNA polymerase II-based promoters, appear to be preferential. However, their application in clinical practice remains questionable. Therefore, vaccination against flaviviruses is still mainly achieved by using either inactivated or live-attenuated vaccines (INVs and LAVs, respectively).

Recent studies suggested that flavivirus structural proteins are dispensable for the RNA genome replication. They can be either completely or partially deleted and such RNAs (replicons) remain self-replicating and capable of expressing not only the nonstructural, but also remaining structural and/or additional heterologous genes. For example, the flavivirus genomes lacking a functional capsid gene, but having the other structural genes intact were synthesized in vitro and used directly for immunization. Their replication led to the subviral particle production and ultimately induced a protective immune response. Application of the modified flaviviruses that are incapable of developing productive, spreading infection is a new means of designing safe and effective in producing protective immunity vaccines (Aberle et al., 2005; Kofler et al., 2004). However, their application probably requires an improvement of the delivery of the in vitro synthesized RNAs into the cells susceptible for RNA replication. This can be achieved by using the most natural approach, by packaging these defective genomes into infectious particles composed by viral structural proteins.

Despite a great concern for flavivirus-associated diseases and continuing spread of the flaviviruses into the new areas, antiviral therapeutics have not been developed yet for these infections, and a very limited number of approved vaccines have been produced to-date. Inactivated viral vaccines (INV) have been licensed to prevent tick-borne encephalitis (TBEV) and Japanese encephalitis (JEV). However, like other inactivated viral vaccines, these vaccines have limited potency, require multiple vaccinations and are expensive to produce. Despite these drawbacks the Japanese encephalitis and tick-borne encephalitis inactivated viral vaccines have a good safety record, and have not been associated with development of any disease. The only licensed live-attenuated vaccine (LAV) for a flavivirus is the widely utilized yellow fever virus (YFV) 17D strain that was developed by serial passaging of the wt Asibi strain of yellow fever virus in chicken embryo tissues. Although this live-attenuated vaccine is considered very safe and effective, there have been cases of yellow fever and adverse effects detected in vaccines, including a recent case in a US military recruit.

The development of the reverse genetics systems for flaviviruses has opened an opportunity for the designing of new types of live-attenuated vaccine, based on rational attenuation of these viruses. This new class of vaccines includes YFV 17D-based chimeras in which the yellow fever virus prM-E-encoding genome fragment has been replaced with the prM-E-cassette derived from heterologous flaviviruses. Similar chimeric virus-based approach was applied for dengue- and tick-borne encephalitis-based backbones. In most cases, chimeric flaviviruses demonstrate a highly attenuated phenotype, but are capable of eliciting efficient protective immune response and protect against following infection with viruses, whose structural proteins are expressed by the chimeras. Vaccination with these chimeric vaccine candidates is not prevented by pre-existing "vector" immunity, which has interfered with potency of recombinant viral vaccines based on other viral vectors.

Although chimeric flaviviruses appear to provide a reasonably universal approach to producing new vaccines, there are concerns that the chimeras themselves will be pathogenic at least in the immunocompromised individuals, or that pathogenic chimeras may arise since mutations have been detected during the process of propagation of these viruses that will be needed to prepare vaccines.

Thus, prior art is deficient is deficient in a safe, potent and effective type of vaccine that can be used against the Flavivirus genus. The present invention fulfills this long-standing need and desire in the art.

SUMMARY OF THE INVENTION

In one embodiment of the present invention, there is a provided a two-component genome flavivirus. Such a flavivirus comprises a pseudoinfectious viral genome encoding cis-acting promoter elements required for RNA replication, envelope proteins and a complete set of non-structural proteins of the flavivirus and does not encode capsid protein of the flavivirus. Additionally, it also comprises a complementing genome encoding cis-acting promoter elements required for RNA replication, capsid protein and a complete set of non-structural proteins of the flavivirus and does not encode envelope proteins of the flavivirus.

In a further related embodiment of the present invention, there is provided a cell culture system infected with the two-component genome flavivirus described supra.

In yet another related embodiment of the present invention, there is provided a method of large-scale propagation of a two-component genome flavivirus. Such a method comprises infecting a cell culture system with the two-component genome flavivirus described supra effective to enable replication of both the genomes in the same cell and release of the two-component flavivirus, thereby enabling large-scale propagation of the two-component genome flavivirus.

In another related embodiment of the present invention, there is provided an immunogenic composition comprising the two-component genome flavivirus described supra, an adjuvant, a pharmaceutically acceptable carrier or combinations thereof.

In yet another related embodiment of the present invention, there is provided a method of protecting a subject from infections resulting from exposure to a flavivirus. Such a method comprises administering an immunologically effective amount of the immunogenic composition described supra to the subject, where the composition elicits an immune response against the flavivirus in the subject, thereby protecting the subject from infections resulting from exposure to the flavivirus.

BRIEF DESCRIPTION OF THE DRAWINGS

Figures 1A, 1B, 1C:
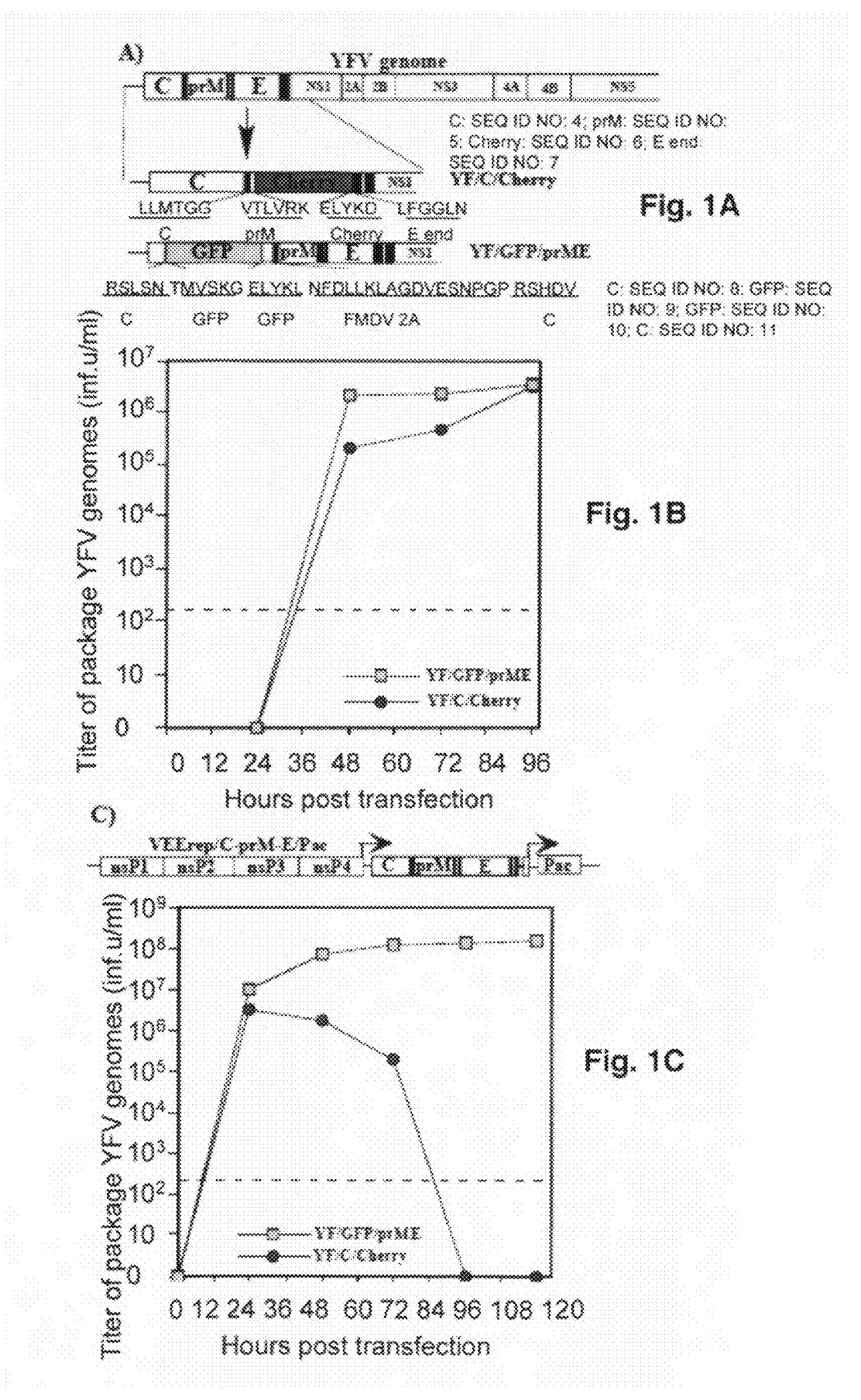

FIGS. 1A-1C show packaging of capsid and prM/E-coding defective YFV genomes into infectious viral particles. FIG. 1A is a schematic representation of the 5' terminal sequences in the replication deficient YFV genomes. The positions of signal peptides and transmembrane domains are indicated by filled boxes. FIG. 1B shows the release of the defective genome-containing viral particles from the cells co-transfected by the in vitro-synthesized RNAs. Media were replaced at the indicated time points and titers were determined as described herein.

FIGS. 2A-2B show replication of YFV with duplicated capsid-specific sequence. FIG. 2A is a schematic representation of recombinant YFV genomes. The codon-optimized capsid-coding sequences are indicated in grey. The alternative ORF in capsid of YF/Cfrs/GFP/C genome that results from introduction of two frame-shift mutations is indicated by filled box. Titers and CPE development were evaluated at 72 h post transfection of the in vitro-synthesized RNAs. FIG. 2B shows analysis of the recombinant viruses released. The in vitro-synthesized RNAs were transfected into the cells, media were replaced at the indicated time points and virus titers were determined using the plaque assay.

FIGS. 3A-3B show selection of YF/C/GFP/C genome-containing variants capable of efficient replication and identification of the adaptive mutations. FIG. 3A is a schematic representation of the YF/C/GFP/C genome and the deletions identified in the efficiently replicating variants. Numbers indicate the positions of the deletions in the amino acid sequence of capsid and GFP proteins. FIG. 3B shows replication of the reconstructed deletion mutants in BHK-21 cells. The in vitro-synthesized RNAs were transfected into cells and media were replaced at the indicated time points. Titers of the released viruses were determined in plaque assay as described herein. Dashed line represents the limit of detection.

FIG. 4A shows a schematic representation of the recombinant genome and sequence of the ORFs located upstream of the GFP gene. The codon-optimized capsid-coding sequence is indicated in grey color. Arrow indicates the start of the GFP-coding sequence. The low case letters indicate the mutations made in the capsid and GFP sequences. FIG. 4B shows replication of designed YFV variants in BHK-21 cells. The in vitro synthesized viral RNAs were transfected into cells and media were replaced at the indicated time points. Titers of the released viruses were determined in plaque assay as described herein. Dashed line represents the limit of detection. FIG. 4C shows titers of the recombinant $YF_{mut}$/GFP virus after serial passaging in BHK-21 cells.

FIGS. 5A-5F show analysis of the two-component genome virus replication. FIG. 5A is a schematic representation of the YFV capsid- and prM/E-coding genomes that are capable of trans complementation during replication in the same cell. The codon-optimized capsid-coding gene is shown in grey color. FIG. 5B shows release of the defective genome-containing viral particles from the cells co-transfected by the in vitro-synthesized RNAs. Media were replaced at the indicated time points and titers of the infectious viral particles, containing each of the genome were determined as described herein. FIG. 5C shows replication of the two-component genome YFV during passaging at an MOI of ~10 inf.u/cell. Media were replaced at the indicated time points and titers of the released infectious particles containing each of the genomes were determined as described herein. FIG. 5D shows replication of the two-component genome YFV after infecting cells at different MOIs. Media were replaced at the indicated time points and the titers of the released infectious particles were determined as described herein. FIG. 5E shows replication of both defective genomes in the infected cells. BHK-21 cells were infected with two-component genome YFV at an MOI of ~1 inf.u/cell and replication of the genomes was evaluated at 48 h post infection. Panel (a) represents cells containing replicating YF/Cherry/Cco; panel (b) shows cells with replicating YF/GFP/prME genome and panel (c) is an overlay. FIG. 5F shows analysis of infectious virus and VLP release from the cells transfected with different YFV-specific RNAs. BHK-21 cells were transfected with the indicated RNAs. At 24 h post transfection, media was replaced with serum-free media that was harvested 24 h later. Particles were pelleted by ultracentrifugation and further analyzed on the discontinuous sucrose gradients as described herein. Presence of YFV-specific proteins in the fractions was detected by Western blotting using D1-4G2 MAB that recognize viral E protein.

Figures 6A, 6B, 6C:
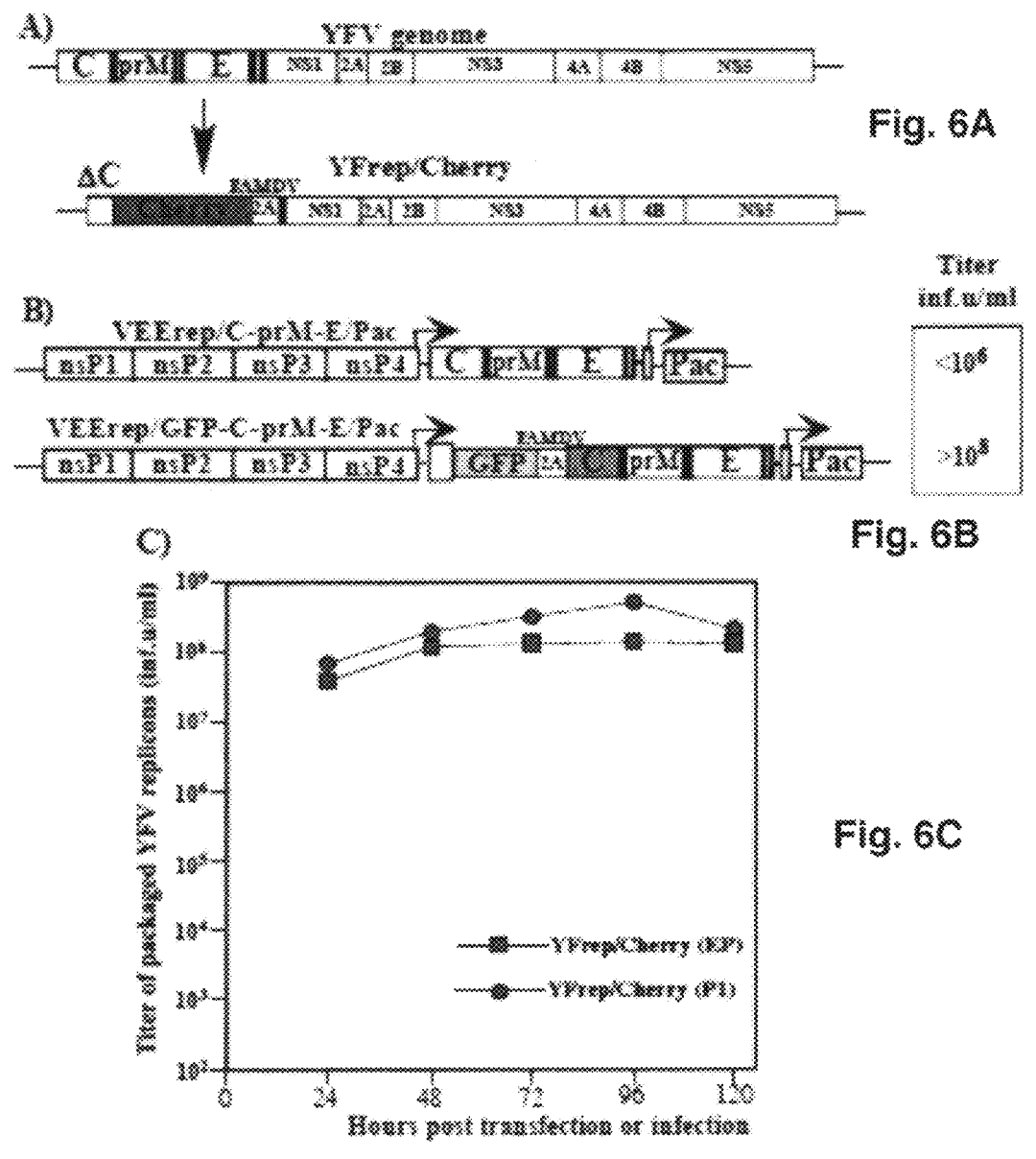

FIGS. 6A-6C show packaging of YFV replicon lacking all of the structural genes in the packaging cell line. FIG. 6A is a schematic representation of YFV replicon encoding fluorescent marker, Cherry instead of the structural proteins. FIG. 6B is a schematic representation of the previously described VEE replicon encoding C-prM-E and its new version. Titers of packaged Yfrep/Cherry in the packaging cell lines developed using both of the VEEV replicons are indicated. FIG. 6C shows release of the infectious, Yfrep/Cherry genome-containing viral particles from the VEErep/GFP-C-prM-E/Pac-containing cells transfected with the indicated YF replicon or infected with the same particles at the next passage. Media was replaced at the indicated time points and titers of the released packaged replicons was determined as described herein.

FIG. 7 shows proposed replication strategies of the two-component genome virus at high and low MOIs. At high MOI, both genomes, the PIV genome (encoding prM/E) and complementing genome (encoding capsid) are delivered to the same cell and produce a complete set of proteins required for virus replication. Cells produce a two-component genome virus that can be further passaged at an escalating scale. At low MOI, cells receive only one of the two genomes and those infected with PIV produce SVPs containing no genetic material and nucleocapsid.

DETAILED DESCRIPTION OF THE INVENTION

Figures 4A, 4B, 4C:
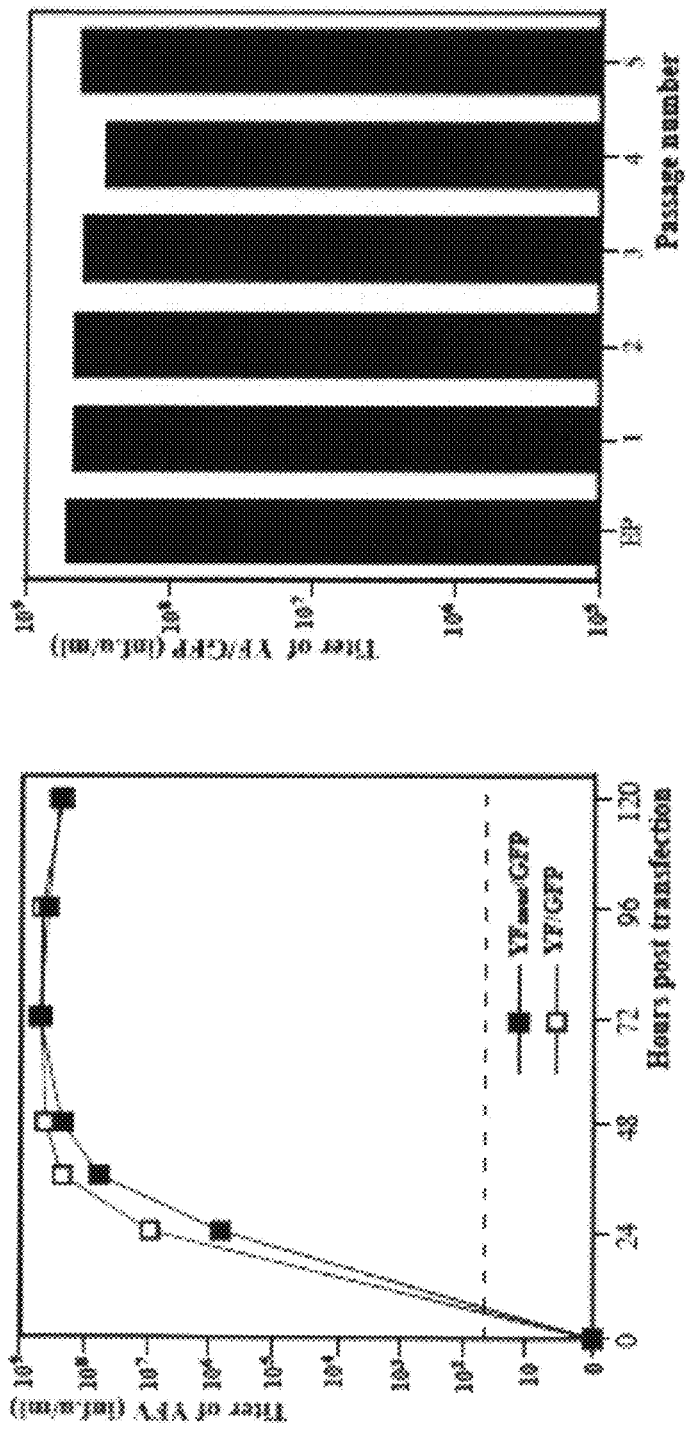
FIGS. 4A-4C show replication of recombinant YFV genomes encoding heterologous gene upstream of the polyprotein.

The goal of the present invention was to develop a new type of replication-deficient flavivirus that could be used as a preventive vaccine against flavivirus-associated diseases. In this regard, the present invention discloses a two-component genome flavivirus, for instance, yellow fever virus (YFV) where the genome of the flavivirus is separated on two genomes. Both of these genomes were deficient in expression of at least one of the proteins required for productive replication (capsid or prM/E) but complemented each other's functions upon delivery into the same cell. These replication defective flaviviruses could be produced at industrial levels for their further application as vaccines against flavivirus infections since they are infectious and capable of performing a single round of infection upon infecting animals. In these animals, cells infected with particles containing only one of the genomes, produce viral nonstructural and an incomplete set of structural proteins. Synthesized prM/E proteins form only the subviral particles that lack genetic material, but function as efficient immunogens. Thus, these defective flaviviruses would combine the safety of the inactivated vaccines with the efficacy and scalability of the live attenuated vaccines. Additionally, these defective flaviviruses were not only capable of producing SVPs but also of expressing heterologous proteins.

To date flaviviruses remain one of the main public health concerns. They are widely distributed in both hemispheres and cause a variety of human-associated diseases. However, safe and efficient vaccines are produced against a handful of flavivirus infections. These vaccines can be characterized as either live-attenuated or inactivated. The only licensed live-attenuated vaccine for a flavivirus is the widely utilized yellow fever virus 17D strain that was developed by serial passaging of the wt Asibi strain of yellow fever virus in chicken embryo tissues. Live-attenuated vaccines were developed against JEV, TBEV, and YFV, but no licensed products were produced against other flaviviruses, such as dengue and WNE. Live vaccines appear to be more efficient than the inactivated viruses or subunit vaccines. However, the obvious safety concerns remain because of the possibility of the reversion to pathogenic phenotype. Application of inactivated vaccines usually requires multiple vaccinations and production of large amounts of material and the need for high-containment facilities to propagate the virulent viruses used for making inactivated products. Thus, although there are promising candidates for both types of flavivirus vaccines, there is no universal approach for their development.

The distinguishing feature of flaviviruses is in the ability of the envelope proteins to form so-called subviral particles (SVPs). Such particles can be efficiently produced by the eukaryotic cells containing standard, prM/E glycoproteins-expressing vectors, or by the defective flavivirus genomes having capsid gene deleted. These virus like particles lack the genetic material and the entire nucleocapsid, but function as efficient immunogen and induce a protective immune response against following infection with the replication competent flaviviruses. The defective flavivirus genomes lacking capsid-coding sequence can be either delivered into the cells in the RNA form or packaged into infectious viral particles using packaging cell lines, in which capsid is supplied in trans by, for example, the persistently replicating alphavirus replicons encoding flavivirus capsid gene under control of the subgenomic promoter. Upon infection of the naïve cells both in vitro and in vivo, these pseudoinfectious flaviviruses are capable of replication and SVP production, but do not develop spreading, productive infection. Therefore, their application does not lead to disease development, and they represent an interesting intermediate between live and inactivated viruses. They perform a single round of infection lading to induction of efficient immune response, and are termed as pseudoinfectious viruses (PIVs).

The development of the reverse genetics systems for flaviviruses has opened an opportunity for the designing of new types of live-attenuated vaccine, based on rational attenuation of these viruses. This new class of vaccines includes yellow fever virus 17D-based chimeras, in which the yellow fever virus prM-E-encoding genome fragment has been replaced with the prM/E-cassette derived from heterologous flaviviruses. These chimeric flaviviruses appear to provide a reasonably universal approach to producing new vaccines. However, there are concerns that the chimeras themselves will be pathogenic at least in the immunocompromised individuals, and the pathogenic chimeras may arise during replication in the immunized vertebrates, or the recombinant, replication-competent flaviviruses would be transmitted by mosquitoes or ticks.

Another promising direction in vaccine development is based on creating unrepairable deletions in flavivirus genome that make productive virus replication in the vaccinated host either a less efficient or impossible event. In the latter case, viral genomes encoding the entire replicative machinery, but lacking, for instance, the C-coding region, can be delivered for the in vivo immunization either as in vitro-synthesized RNA, capable of self-replication. Direct immunization with in vitro synthesized defective RNA genomes, which specifies the production of subviral particles (SVPs) in the absence of a complete viral replication cycle, has been demonstrated to be safe and effective in producing protective immunity. However, there may be significant obstacles to producing an RNA-based vaccine candidate, due to synthesis, stability, and delivery issues. Thus, the previous methods for development of flavivirus vaccines were based in preparing either inactivated viral vaccines that are very safe, but have limited potency and require multiple vaccinations or live-attenuated vaccines that have strong potential for the reversion to a wild-type, pathogenic phenotype and transmission by arthropod vectors.

Furthermore, application of PIVs for vaccine purposes requires their large-scale production and the development of the cell lines that package the defective genomes into infectious virions demonstrated this possibility. PIVs can be passaged in the packaging cell lines, but not in the naïve cells, at an escalating scale. However, this appears to be not the only means of their large-scale propagation. The production of flaviviruses of the present invention did not require development of such cell lines but the method discussed herein led to efficient PIV production. Additionally, the replication deficient flaviviruses of the present invention are not only safe to use but are also capable of replicating in tissue culture at an escalating, industrial scale and expressing additional genes. Thus, these flaviviruses are deficient in replication and incapable of causing productive, spreading infection in humans and animals.

In general, the genetic material required for virus replication was separated between two genomes capable of transcomplementing each other's deficiencies. Both of them encoded the cis-acting promoter elements required for RNA replication and the complete set of the nonstructural proteins that form the replicative enzyme complex. Thus, both RNA genomes are capable of self-replication, but one of them encodes capsid and has the genes encoding the envelope proteins deleted, and the second one encodes the envelope genes, but not a capsid.

Figure 7:
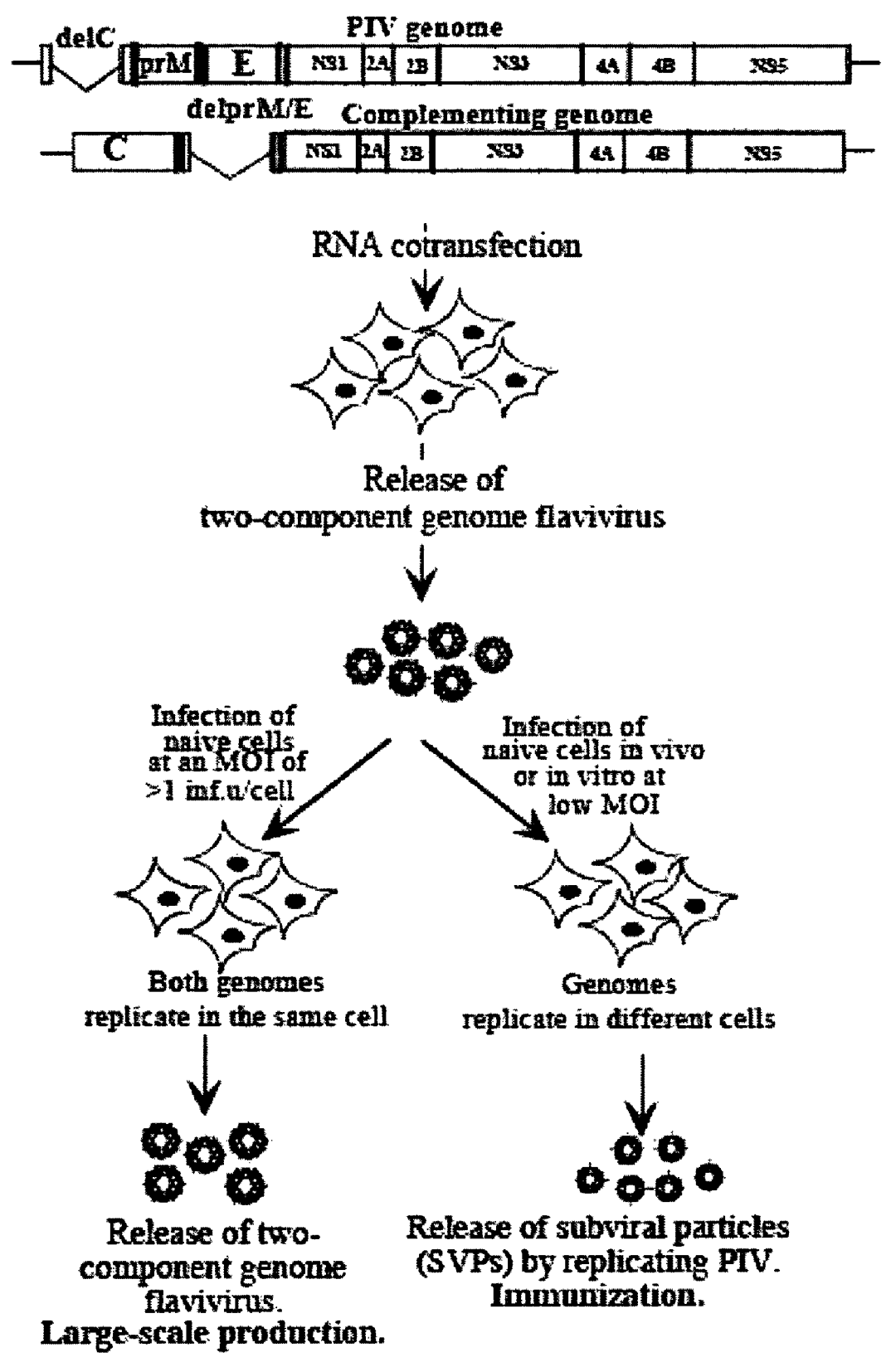

Upon delivery into the same cell, both genomes produce the entire set of the structural proteins, and cells release high titers of infectious viral particles having each of the genomes. At the next passage, the naïve cells can be infected with the viruses at an MOI that allows both genomes to be delivered into the same cell. This leads to a development of productive replication and release of infectious viral particles, containing each of the genomes. Thus, this system allows propagation of the recombinant viruses at an escalating scale. Upon inoculation into the animals (that have a very high number of susceptible cells), each of the genomes is delivered into different cells, the spreading infection becomes an impossible event, and cells infected with the virions having the genomes encoding the envelope proteins, produce noninfectious, virus-like particles that lack of the genetic material but serve as efficient immunogens and induce a protective immune response against following infection with the wild type virus (FIG. 7).

To promote efficient replication and complementation, both defective genomes require presence of the 5'UTR and more than 60 nt (Element 1) of the following, natural protein-coding sequence represented by the amino-terminal fragment of capsid for the majority of flaviviruses or $N^{pro}$ gene for the members of the pestivirus genus. This sequence is followed by either ubiquitine or foot-and-mouth disease virus (FAMDV)-specific 2A protease, fused with either capsid- or envelope proteins-coding sequence. This combination of fused genes is essential for replicaton of both genomes and their packaging with equal efficiency into viral particles.

The use of artificial, codon-optimized sequences encoding viral structural proteins excludes the possibility of recombination between two defective viral genomes that might potentially lead to formation of the replication-competent flaviviruses. Both defective genomes can be used for expression of the additional genes and, thus, serve as vectors for generating the immune response for heterologous proteins. The additional genes can be cloned between the sequence of Element 1 and ubiquitine or FAMDV 2A protease.

As discussed supra, application of these two-component genome flaviviruses for vaccination does not lead to development of productive, spreading infection in the immunized humans and animals. Since humans and animals have large number of cells, these cells are infected at a very low multiplicity and this leads to infection with one of the genomes only. Such cells are capable of producing only so-called virus-like particles that lack nucleocapsid and any genetic material. The latter particles serve as efficient immunogen, but are incapable of performing the next rounds of infection. It is also contemplated herein that the defective viral genomes with trans-complementing functions can express additional genetic information and serve as multivalent vaccines.

Specifically, the present invention used the genetic material of yellow fever virus to demonstrate the efficacy of the method discussed supra. In this regard, the genetic material of yellow fever virus was separated between two viral genomes capable of transcomplementing each others deficiencies. Each of the originally designed defective YFV genomes encoded the entire RNA replicative machinery, and one of them had a deletion of almost entire capsid gene, and the second genome encoded no prM/E. To follow the replication of each genomes in tissue culture and to measure the titers of the infectious particles, the genomes encoded different fluorescent markers, GFP and Cherry. Their expression in the cells indicated the infection and replication of the particular genome. Upon delivery to the same cells, the YF/GFP/prME and YF/C/Cherry were expected to produce the entire set of viral structural proteins and, ultimately, be packaged into infectious virions. However, surprisingly, the initial attempts to establish productive replication were unsuccessful due to high cytotoxicity of the YF/C/Cherry replication. It produced very high levels of fluorescent protein, but also caused a robust CPE that resulted in a low-level release of the infectious viral particles.

To further understand this phenomenon, an YFV genome that encoded two copies of capsid gene was designed, where one of them could be exploited for extensive genetic manipulations. This virus was also unusually cytotoxic and replicated to low titers. Following modifications of the capsid-coding sequence strongly indicated that the increase in the cytotoxicity was caused by capsid protein itself (when it was expressed not in the context of C-prM-E cassette), rather than by the possible changes in the RNA secondary structure (FIG. 2). Moreover, YF/C/GFP/C virus having two copies of capsid gene in the genome could further evolve and develop variants adapted for growth to higher titers with lower levels of CPE development. To date the exact mechanism of the effect of YFV capsid expression by YF/C/Cherry or YF/C/GFP/C viruses on CPE induction remains unclear.

Sequencing of the YF/C/GFP/C variants adapted to higher level of virus release provided the means of generating modified infectious viruses capable of stable expression of additional heterologous proteins in vivo and in vitro. However, most importantly, the identified spontaneous deletions presented an opportunity to modify the originally designed defective in replication YF/C/Cherry virus genome into YF/Cherry/Cco that had a different protein-coding strategy and was capable of efficient trans-complementation of the YF/GFP/prME replication. Cells co-transfected with the in vitro-synthesized RNA of both genomes produced viral particles, in which both capsid or prME encoding genomes were present at the same concentration, and this unusual virus could be further passaged in naïve cells at an escalating scale.

Infection of cells at low MOIs unambiguously demonstrated that both genomes were packaged into separate viral particles, therefore this YFV, having two genomes with complementary functions, cannot be termed as a segmented genome virus (that suppose to have all of the genome fragments packaged into the same virion), but rather a two-component genome virus. Viruses of such type, having both genome segments packaged separately, were previously described in plants. Further application of such viruses for immunization might raise a concern about possible recombination between two genomes that could lead to formation of the infectious, complete, replication competent virus. Therefore, in spite this is a highly unlikely event, the capsid gene in the YF/Cherry/C RNA was represented by a synthetic, codon-optimized version, lacking the cyclization sequence. In multiple experiments with two-component genome YFV, the formation of the infectious YFV having the unfragmented genome was not detected. However, it is possible to additionally reduce possibility of recombination by using different pairs of cyclization sequences in the capsid- and prME-encoding, self-replicating fragments.

Interestingly, modification of the C-prM-E coding strategy in the not YFV genome-based constructs led to dramatic increase of packaging of the YFV vectors that encode no structural proteins at all. The cell lines producing 25 a.a. of C-GFP-Copt-prM-E from the persistently replicating VEErep/GFP-C-prM-E/Pac packaged YFV replicons to dramatically higher titers than similar cell lines expressing C-prM-E cassette only. Packaged YFV replicons were not only released to the titers above $10^8$ inf.u/ml, but could be also passaged in this packaging cell line without decrease in titers. Thus, simple modification of C-prM-E coding subgenomic RNA by cloning 25 capsid-specific codons upstream of structural polyprotein had a very strong positive impact on infectious particles release and might widen the number of YFV-based vectors for delivery and expression of heterologous genetic information. It is contemplated that the designed unusual strategy of C-prM-E expression leads to different compartmentalization of the translated structural proteins that promotes the infectious virions formation.

In conclusion, the results discussed supra suggest that YF PIV, capable of prM/E expression, and, most likely, PIVs, derived from other flaviviruses, can be passaged in tissue culture using another defective in replication, capsid-producing flavivirus genome (FIG. 7). During replication in the same cell, these two defective genomes produce a complete set of viral structural proteins and are efficiently packaged into separate infectious viral particles that can be characterized as a two-component genome virus. As demonstrated previously, PIVs serve as efficient immunogens, and, thus, the two-component genome virus might be applied for development of recombinant flavivirus-specific vaccines (FIG. 7). These vaccines will be cheaper than the inactivated vaccines and safer than live attenuated vaccines. Expression of capsid from YFV genome having the deleted prM/E genes, required additional modification of the 5' terminal sequence, and cloning an additional capsid-specific sequence. Application of the same modifications to the replication-competent YFV led to development of virus that is capable of expressing additional genetic information. Modification of the YFV C-prM-E expression cassettes in the VEEV replicons used for generating packaging cell lines drastically improved packaging YFV-based vectors. Separation of capsid-coding sequence and the promoter elements either in the YFV genome or in the capsid-coding, defective in replication YFV genome provides an opportunity for expression of the structural genes, derived from heterologous flaviviruses, independently of the cyclization signal and represents a possible means for studying the mechanism of the packaging process.

The present invention contemplates producing and evaluating new types of RepliVAX constructs, including but not limited to:

(1) Two-component genome particle production (including removal of reporter genes from existing constructs) and assay systems. RepliVAX can be replicated using either stable cell lines or in a unique two-component genome system. In the case of YFV, a system with two defective genomes was developed, one encoding the essential C gene and the red fluorescent protein (Cherry), and the other encoding the prM and E proteins and green fluorescent protein (GFP). Cells co-transfected with the in vitro-synthesized RNA of both genomes produced viral particles, in which either C or prME-encoding genomes were present at the same concentration, and this two-component genome virus could be further passaged in naïve cells at an escalating scale if the MOI exceeded 1 inf.u/cell.

To enhance this system, the reporter genes in both YFV genomes (RepliVAX YF and helper) are deleted to make the two-component genome viruses applicable for animal testing, and develop the cell lines that can be applied for quantitative analysis of the particles containing each of the genomes. The present invention contemplates similar work in generation of WNV. The modified C- and prM/E-encoding genomes are synthesized in vitro and transfected into Vero cells. Methods are developed to quantify the amounts of each genome particle (C or prM/E-encoding) by dilution of the two-component co-cultures followed by focus formation on cell lines that express either C or prM/E proteins. The prM/E-genome-encoding RepliVAX particles are capable of forming foci in the C-producing cells and C-producing "helper" genomes will form foci in the C-producing cell line.

(2) Generation of TBE chimeras: The TBEV prM/E-encoding YFV-based RepliVAX are used. The prM/E-encoding cassette is synthesized from the oligonucleotides, and the sequence is optimized for the most efficient expression by applying the codon frequency derived from the most efficiently translated human mRNAs. Based on the preliminary data, the TBEV signal peptide in prM is replaced by YFV-specific amino acid sequences, since preliminary experiments suggest that such replacements strongly increase viral particle production. These RepliVAX genomes are i) evaluated for the ability to produce SVPs and ii) packaged into TBEV envelope by using both packaging Vero cell lines, expressing TBEV capsid and two-component genome-based packaging system, in which the second defective genome express the codon-optimized TBEV C.

In addition to this, the present invention contemplates developing transencapsidation systems: The present invention contemplates developing trans-packaging systems for YFV RepliVAX platforms. A universal system for packaging RepliVAX YF into the envelopes is developed that will be the most efficient in infecting the dendritic cells and, consequently, the antigen presentation. This packaging is independent of the flavivirus glycoproteins, encoded by the RepliVAX genomes. This trans-packaging system is expected to overcome possible inefficient infection resulting from the use of DEN glycoproteins and the difference in the immune response induced by the RepliVAX genomes encoding envelope glycoproteins derived from different DEN viruses.

The present invention contemplates examining: i) different packaging strategies (packaging cell lines versus two-component genomes) for the most efficient infectious particles production; ii) proteins derived from different DEN viruses (DEN1 and DEN2); iii) the efficiency of the large-scale production of packaged RepliVAX genomes in Vero cells; iv) stability of DEN cassettes during following passaging; and v) the efficiency of the immune response induced in mice against DEN1 and 2 after RepliVax immunization.

The present invention also contemplates packaging TBEV prM/E-encoding RepliVAX YF into the homologous, YFV, structural proteins. The preliminary data strongly indicate that such packaging is efficient and, its further development might ultimately lead to the development of the universal packaging systems for RepliVAX genomes encoding any heterologous prM/E cassettes.

The present invention is directed to a two-component genome flavivirus, comprising a pseuoinfectious viral genome encoding cis-acting promoter elements required for RNA replication, envelope proteins and a complete set of non-structural proteins of the flavivirus and not encoding capsid proteins of the flavivirus; and a complementing genome encoding cis-acting promoter elements required for RNA replication, capsid protein and a complete set of non-structural proteins of the flavivirus and not encoding envelope proteins of the flavivirus. Additionally, the pseudoinfectious viral genome and the complementing genome must also encode a 5' UTR and an amino terminal fragment of the capsid protein open reading frame that contains a cyclization sequence that is essential for RNA replication. Furthermore, the pseudoinfectious viral genome or the complementing genome may comprise a ubiquitine or a foot-and-mouth disease (FAMDV)-specific 2A protease fused to the sequence encoding the envelope proteins or the capsid protein. Additionally, the pseudoinfectious viral genome and the complementing genome may further comprise additional genetic material comprising structural genes of other viruses, bacteria or parasites, wherein expression of the genes induce immune response against infections caused by the viruses, the bacteria or the parasites. Representative examples of the flavivirus may include but is not limited to yellow fever virus, West Nile virus, dengue virus, tick-borne encephalitis virus, Saint Louis encephalitis virus, Japanese encephalitis virus, Murray Valley encephalitis virus, classical swine fever virus or hepatitis C virus.

The present invention is also directed to a cell culture system infected with the two-component genome flavivirus described herein. Representative examples of the cell culture system may include but is not limited to Vero, BHK-21, C7/10 or other cells of vertebrate and mosquito origin.

The present invention is further directed to a method of large-scale propagation of two-component genome flavivirus, comprising: infecting a cell culture system with the two-component genome flavivirus described supra effective to enable replication of both the genomes in the same cell; and release of the two-component genome flavivirus, thereby enabling large-scale propagation of the two-component genome flavivirus. Generally, the cell culture system is infected with the two-component genome flavivirus at a multiplicity of infection of more than 1 infectious unit/cell. Additionally, the replication deficient flavivirus is defective in replication, incapable of causing disease, infectious and capable of performing a single round of infection in vivo.

The present invention is still further directed to an immunogenic composition, comprising: the two-component genome flavivirus described supra, an adjuvant, a pharmaceutically acceptable carrier or combinations thereof.

The present invention is also directed to a method of protecting a subject from infections resulting from exposure to a flavivirus, comprising: administering an immunologically effective amount of the immunogenic composition described supra to the subject, where the composition elicits an immune response against the flavivirus in the subject, thereby protecting the subject from infections resulting from exposure to the flavivirus. Additionally, the administration may be via intraperitoneal, intradermal, subcutaneous, intramuscular, oral or intranasal route. Examples of the flavivirus may include but is not limited to yellow fever virus, West Nile virus, dengue virus, tick-borne encephalitis virus, Saint Louis encephalitis virus, Japanese encephalitis virus, Murray Valley encephalitis virus, classical swine fever virus or hepatitis C virus.

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "immunologically effective amount" refers to an amount that results in an improvement or remediation of the symptoms of the disease or condition due to induction of an immune response. Those of skill in the art understand that the effective amount may improve the patient's or subject's condition, but may not be a complete cure of the disease and/or condition.

As used herein, "adjuvant" is defined as a substance which when included in a vaccine formulation non-specifically enhances the immune response to an antigen.

The immunogenic composition disclosed herein may be administered either alone or in combination with another drug, a compound, or an antibiotic. Such a drug, compound or antibiotic may be administered concurrently or sequentially with the immunogenic composition disclosed herein. The effect of co-administration with the immunogenic composition is to lower the dosage of the drug, the compound or the antibiotic normally required that is known to have at least a minimal pharmacological or therapeutic effect against the disease that is being treated. Concomitantly, toxicity of the drug, the compound or the antibiotic to normal cells, tissues and organs is reduced without reducing, ameliorating, eliminating or otherwise interfering with any cytotoxic, cytostatic, apoptotic or other killing or inhibitory therapeutic effect of the drug, compound or antibiotic.

The composition described herein and the drug, compound, or antibiotic may be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The immunogenic composition described herein and the drug, compound or antibiotic may be administered independently one or more times to achieve, maintain or improve upon a therapeutic effect. It is well within the skill of an artisan to determine dosage or whether a suitable dosage of the immunogenic composition and the drug, compound or antibiotic comprises a single administered dose or multiple administered doses.

As is well known in the art, a specific dose level of such an immunogenic composition for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

Administration of the immunogenic composition of the present invention to a subject will follow general protocols for the administration of therapies used in treatment of bacterial infections taking into account the toxicity, if any, of the components in the immunogenic composition, and/or in embodiments of combination therapy, the toxicity of the antibiotic. It is expected that the treatment cycles would be repeated as necessary. It also is contemplated that various standard therapies, as well as surgical intervention, may be applied in combination with the described therapy.

As is known to one of skill in the art the immunogenic composition described herein may be administered along with any of the known pharmacologically acceptable carriers. Additionally the immunogenic composition can be administered via any of the known routes of administration such as subcutaneous, intranasal or mucosal. Furthermore, the dosage of the composition to be administered can be determined by performing experiments as is known to one of skill in the art.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Cell Cultures

The BHK-21 cells were provided by Paul Olivo (Washington University, St. Louis, Mo.). They were maintained at 37° C. in alpha minimum essential medium (aMEM) supplemented with 10% fetal bovine serum (FBS) and vitamins.

EXAMPLE 2

Plasmid Constructs

Standard recombinant DNA techniques were used for all plasmid constructions. The parental low-copy number plasmid pACNR/FLYF-17Dx containing infectious cDNA of YFV 17D strain genome was described (Bredenbeek et al., 2003) and provided by Dr. Charles Rice (Rockefeller University, New York).

pYF/GFP/prME contained a defective YFV genome (YF PIV), in which a fragment encoding a. a. 26-100 of YF capsid gene was replaced by codon-optimized GFP gene derived from pEGFP-N1 (Clontech). This plasmid was designed in a previous study, in which it was termed pYF/PIV. pYF/C/Cherry encoded the entire capsid protein, followed by prM signal peptide and 6 a.a. of prM, fused with the Cherry (one of the red fluorescent proteins)-coding sequence. The latter gene was fused in frame with the rest of the YF ORF that started from the transmembrane domain of E protein (see FIG. 1A for details).

Plasmid pYF/C/GFP/C contained the YFV genome, in which the 101 a.a.-long capsid-coding sequence was fused with GFP, followed by 2A protease of foot-and-mouth disease virus (FAMDV 2A), codon-optimized capsid gene and the rest of YF polyprotein prM-NS5-coding sequence. pYF/Cfrs/GFP/C and pYF/Chyb/GFP/C had essentially the same design (FIG. 2A), but, in the pYF/Cfrs/GFP/C, one nucleotide was inserted after nt 202 and nt 422 was deleted, and in pYF/Chyb/GFP/C, the sequence between nt 201 and 422 was replaced by the synthetic gene encoding the same amino acid sequence, but utilizing different codon usage.

pYF/DC/GFP/C and pYF/C/DGFP/C were the derivatives of pYF/C/GFP/C, which contained deletions in the capsid- and GFP-coding sequences, respectively, that were identified in the selected deletion mutants (see FIG. 3A for details). pYF/GFP contained YFV genome, in which the 5'UTR was followed by the ORF encoding 25 a.a. of YFV capsid, fused with GFP and FAMDV 2A and the entire YFV polyprotein C-NS5, in which capsid gene was presented by the codon-optimized version (FIG. 4A). pYF/GFPmut had essentially the same design, but the fragment encoding 25 a.a. of capsid contained 3 one-nt-long insertions and point mutations in the beginning of GFP-coding sequence.

pYF/Cherry/Cco contained a defective YFV genome, in which 75 nt of capsid were fused with Cherry gene, followed by sequence encoding FAMDV 2A protease, codon-optimized capsid with prM signal peptide, 6 a.a. of prM, 49 carboxy terminal a.a. of E protein and the rest of the YFV polypeptide (FIG. 5A). pYFrep/Cherry contained a YFV replicon, in which the structural genes were replaced by Cherry protein-coding sequence. At the amino terminus Cherry was fused with 25 a.a. of YFV capsid, and at the carboxy terminus, it was followed by FAMDV 2A, followed by NS1 signal peptide and the rest of the YFV polyprotein (FIG. 6A).

pVEErep/C-prM-E/Pac plasmid has been described elsewhere. pVEErep/GFP-C-prM-E/Pac plasmid contained VEEV replicon, in which the subgenomic RNA encoded 25 a.a. of YFV capsid, fused with GFP, followed by FMDV 2A protease, codon-optimized YFV capsid and prM/E genes. The second subgenomic promoter was driving the expression of Pac, puromycin acetyltransferase. All of the recombinant viral genomes and replicons were cloned under control of the SP6 RNA polymerase promoter.

EXAMPLE 3

RNA Transcriptions

Plasmids were purified by centrifugation in CsCl gradients. Before the transcription reaction, the YFV genome or replicon-containing plasmids were linearized by XhoI. Plasmids with VEEV replicons were linerized by MluI. RNAs were synthesized by SP6 RNA polymerase in the presence of cap analog as described elsewhere. The yield and integrity of transcripts were analyzed by gel electrophoresis under non-denaturing conditions. Aliquots of transcription reactions were used for electroporation without additional purification.

EXAMPLE 4

RNA Transfections

Electroporation of BHK-21 cells was performed under previously described conditions (Liljestrom et al., 1991). For establishing packaging cell cultures, Pur was added to the media to a concentration of 10 mg/ml at 24 h post electroporation of the VEEV replicons. Transfection of in vitro-synthesized YF PIV genome was performed 5 days later, when replicon-containing cells resumed efficient growth.

EXAMPLE 5

Measuring the Titers of Infectious Viral Particles Containing Defective YFV Genomes For measuring the titers of released virions containing different defective genomes, BHK-21 cells were seeded into six-well Costar dishes at a concentration of $5 \times 10^5$ cells/well. Four hours later, cells were infected with different dilutions of the samples. After 1 h incubation at 37° C. in an 5% $CO_2$ incubator, they were overlaid with 2 ml of aMEM supplemented with 10% FBS. The numbers of infected cells were estimated by counting GFP- and Cherry-positive cells under an inverted UV microscope after 36 h of incubation. The fraction of infected cells from the seed quantity was determined via counting of fluorescence-producing cells in a defined area of microscopic field. Counts for 5 different fields were averaged and recalculated for the titer corresponding to each serial dilution.

Titers of replication-competent viruses were determined by standard placing of the samples on BHK-21 cells (Lemm et al., 1990). After three days incubation at 37° C., monolayers were fixed by 2.5% formaldehyde and stained with crystal violet.

EXAMPLE 6

Passaging of Viruses

Packaging cell lines were established by transfection of the in vitro-synthesized VEEV replicon RNAs, followed by Pur selection. These cell lines were either transfected by the in vitro-synthesized YF replicon RNA or infected with the previously packaged replicons. Samples were harvested at the time points indicated in the description of the figures by replacing the media. Passaging of two-component genome YF viruses was performed by infecting the cells at the MOIs indicated supra. Samples were harvested at the time points indicated in the figures by replacing the media, and titers of particles, containing the defective genomes, were determined as indicated in above. Replication-competent viruses were passaged by infecting naïve BHK-21 cells with 100 µl of virus, harvested at the previous passage. Samples were harvested at 72 h post infection, and titers were determined by plaque assay.

EXAMPLE 7

Analysis of YF SVP Production

BHK-21 cells were transfected by 8 mg of in vitro synthesized YFV 17D or YF/GFP/prME viral genomes, or co-transfected with YF/Cherry/Cco and YF/GFP/prME genomes. After 24 h incubation in 10 ml of aMEM supplemented with 10% FBS, the latter medium was replaced by 10 ml of serum-free medium VP-SF (Invitrogen) that was harvested in 24 h to analyze SVP release. The collected VP-SF samples were clarified by low-speed centrifugation (5,000 r.p.m, 10 min, 4° C.), and then concentrated by ultracentrifugation through 2 ml of 10% sucrose, prepared on PBS, in SW-41 rotor at 39,000 r.p.m, 4° C. for 6 h.

Pellet material was further analyzed in sucrose density gradient as previously described (Schalich et al., 1996). Briefly, the 0.5 ml samples were loaded to the discontinuous sucrose gradient (1.5 ml of 50%, 1.5 ml of 35% and 1.5 ml 10% sucrose prepared on PBS buffer). Centrifugation was performed in SW-55 rotor at 45,000 r.p.m. at 4° C. for 4 h. After fractionation, samples were diluted 3-fold with PBS and SVPs were pelleted by centrifugation in TLA-55 rotor at 45,000 r.p.m. at 4° C. for 1 h in Optima MAX Ultracentrifuge (Beckman). Pellets were dissolved in the loading buffer for SDS-polyacrylamide gel electrophoresis, lacking b-mercaptoethanol (to preserve binding to D1-4G2 MAB) and further analyzed by western blotting. After protein transfer, the nitrocellulose membranes were processed by D1-4G2 MAB, and horseradish peroxidase (HRP)-conjugated secondary donkey anti-mouse antibodies purchased from Santa Cruz Biotechnology. HRP was detected using the Western Blotting Luminol Reagent according to the manufacturer's recommendations (Santa Cruz Biotechnology). Side-by-side gradient analyses were performed with YFV ($2 \times 10^8$ PFU), subjected to the same procedures as described above for YFV-PIV-derived SVPs.

EXAMPLE 8

In Vivo Experiments 6 day-old mice (outbred Swiss Webster, Harlan) were infected by the recombinant YFV at doses indicated in description of the figure by the intracranial (i.c.) route (20 ml volume). Mice were monitored for 8 days for signs of disease and death, than animals that were moribund, and titers in the brains were evaluated by plaque assay.

EXAMPLE 9

Capsid- and prM/E-Expressing Defective YFV Genomes Strongly Differ in the Replication Efficiency In the previous study, a system for trans-complementation of the defects in YFV replication and packaging of the defective genomes into infectious YF viral particles was developed. To achieve this, the cell lines were designed so that they contained VEEV replicons producing either YFV capsid or the entire structural polyprotein that complemented replication of the capsid-deficient YFV genomes. However, the use of alphavirus replicons is not an absolute prerequisite of trans-complementation. Functional capsid can apparently be supplied by other cassettes capable of its production to the level sufficient for flavivirus genome packaging. Therefore, an attempt was made to exclude any heterologous expression vectors from the packaging system and produce capsid from the second YFV genome that lacks the structural genes other than the capsid-coding one.

The PIV genome (YF/GFP/prME) contained a deletion of almost entire capsid-coding sequence and the second, complementing genome (YF/C/Cherry) had the prM/E-coding sequence deleted, and the capsid gene remained intact. To analyze the replication patterns of both genomes in tissue culture, two different fluorescent proteins, GFP and Cherry were cloned into their ORFs (FIG. 1A). Both genomes were expected to be incapable of developing productive, spreading infection because of the inability to produce a complete set of structural proteins. However, they could produce all of the proteins required for viral particles formation while replicating in the same cell.

The in vitro-synthesized RNAs were co-transfected into BHK-21 cells and the expression of both markers, GFP and Cherry, confirmed their replication. Surprisingly, the titers of the released infectious viral particles containing either capsid- or prM/E-encoding genomes were lower than expected, close to $10^6$ inf.u/ml, suggesting that the trans-complementation was inefficient (FIG. 1B). The comparison of GFP and Cherry expression patterns indicated that the capsid-encoding genome replicated dramatically more efficiently than its prM/E-producing counterpart. After electroporation, the expression of Cherry reached detectable levels 18 to 24 h earlier than that of GFP-expressing defective genome, but, most importantly, its replication also caused cell death within 2-3 days post transfection. Rapid CPE development was not a side effect of Cherry protein expression, because the same cassette, in which Cherry was replaced by GFP, demonstrated high cytopathogenicity as well (data not shown).

In the additional experiments, replication of the GFP and Cherry expressing genomes was compared in the previously designed cell line in which the entire YFV structural polyprotein precursor, C-prM-E, was expressed from the VEEV replicon. In agreement with the above-described data, the replication of capsid-expressing YF/C/Cherry genome had a deleterious effect on the cells, and essentially all of the transfected cells were dead within 96 h post transfection (FIG. 1C), and the infectious virus particles were released to lower titers, than found in the media of the same cells transfected with the prM/E-expressing construct, YF/prME/GFP.

As previously described (Mason, Shustov, and Frolov, 2006), the cells bearing YF/prME/GFP did not develop CPE (FIG. 1C) and continued to release packaged viral genomes even after following cell passaging. Thus, the above experiments indicated that either presence of capsid-coding sequence in the YF/C/Cherry genome or expression of capsid protein itself (or both factors together) strongly determined cytopathogenicity of this replicating RNA, and, therefore, created a profound difference in replication of capsid- and prM/E-producing genomes that could be a reason for inefficient trans-complementation. Moreover, transfected cells were likely dead before the release of infectious viral particles to high titer.

EXAMPLE 10

The Effect of Capsid Protein on Replication of YFV Genome RNA

To distinguish between the effects of capsid or capsid-coding sequence on replication of defective YFV-specific RNA was designed, where a set of recombinant YFV genomes, in which the sequences encoding the entire polyprotein that includes all of the structural and nonstructural genes, and the 5'-terminal sequences that contains the RNA promoter elements that are required for replication were separated. To achieve this, a natural capsid gene in the polyprotein was replaced with its codon-optimized version (Cco) having a mutated cyclization sequence that was incapable of functioning in the RNA replication. Then, the YFV 5'UTR was cloned upstream of Cco followed by sequence encoding the natural capsid without prM-specific signal peptide, fused with GFP and FAMDV 2A protease genes. Thus, the upstream capsid gene contained a cyclization signal essential for RNA replication, and the initiating methionine codon.

In the final construct YF/C/GFP/C, the ORF started from this initiating AUG and continued through the entire polyprotein. The Cco a.a. sequence differed from that of the natural YFV capsid only by having a proline as a first a.a., because it was required for FAMDV 2A-specific processing. This experimental system allowed performing a wide variety of manipulations in the 5' terminus, including extensive modifications in the amino-terminal, natural capsid-coding part of the ORF, without affecting the functional capsid protein (Cco) expression. Therefore, in another cassette, YF/Cfrs/GFP/C, the first capsid contained a 1 nt insertion after nt 202 and 1 nt deletion after nt 421. These modifications were made in a way to save the computer predicted secondary structure of the 5' end of viral genome and 3' end of the negative strand RNA, however, they changed the sequence of a 73 a.a.-long peptide that covers a large capsid fragment.

In the third construct, YF/Chyb/GFP/C, the first capsid gene was a hybrid between the natural and codon-optimized sequences. It encoded a wt protein, but the RNA sequence downstream from the circulation signal, starting from nt 202, was different from that in the wt YFV genome. Thus, the 5' termini of recombinant viral genomes encoded either i) the natural capsid gene fused with GFP(YF/C/GFP/C), or ii) almost natural RNA sequence (having only two frame-shift mutations), but strongly modified protein (YF/Cfrs/GFP/C), or iii) modified RNA sequence, but natural protein (YF/Chyb/GFP/C). All three RNAs and the RNA of the YF 17D genome were synthesized in vitro and equal amounts were transfected into BHK-21 cells.

Figures 2A, 2B:
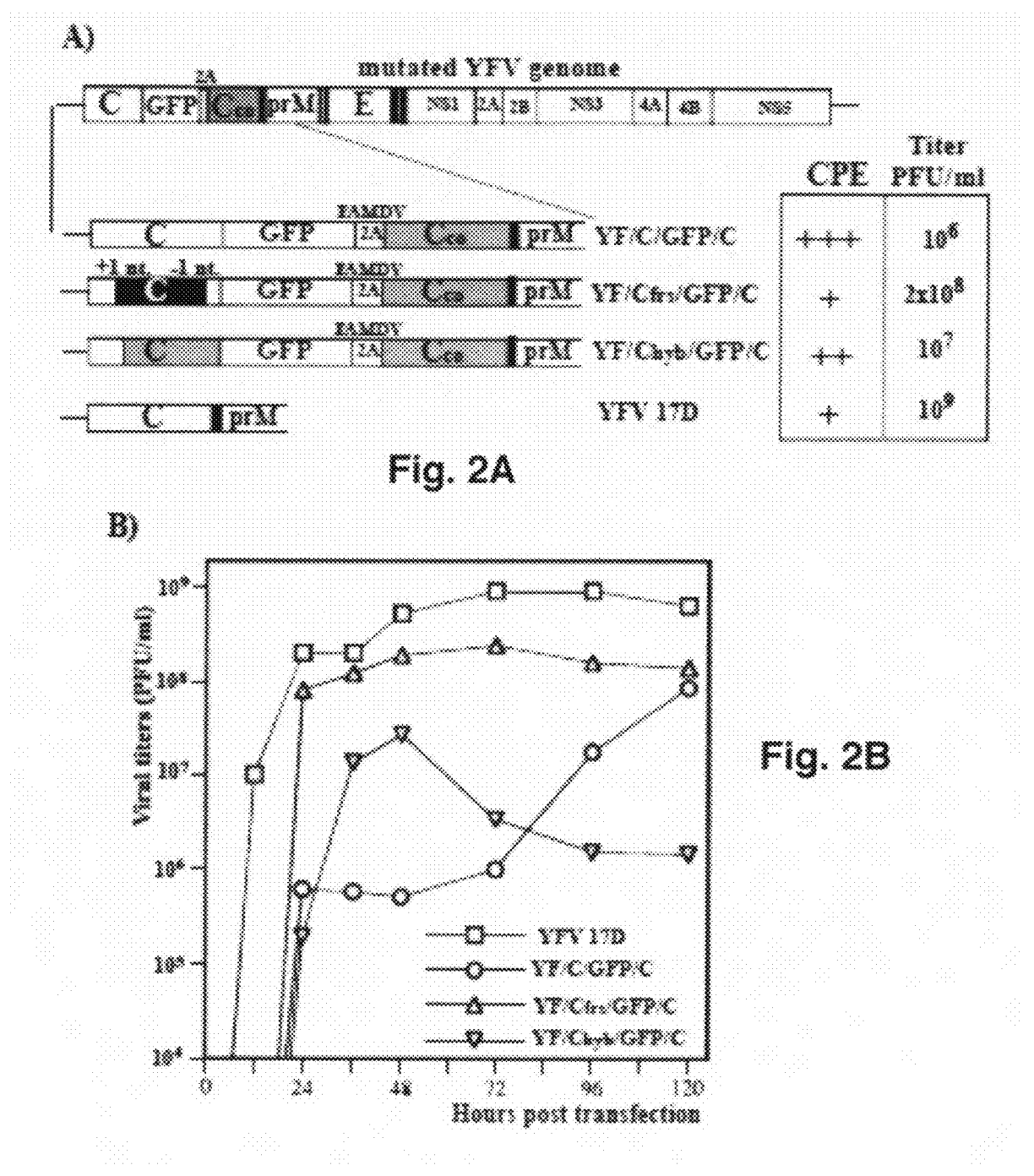

The analysis of infectious virus release demonstrated that only the construct expressing mutated first capsid, YF/Cfrs/GFP/C, was capable of efficient replication to the titers comparable to those achieved by the YFV 17D (FIG. 2B). However, the difference in replication rates was still noticeable. YF/Chyb/GFP/C and especially YF/C/GFP/C, both genomes expressing wt capsid fused with GFP, demonstrated highly cytopathic phenotype and dramatic decrease in titers of infectious virus release, in spite of the fact that they expressed GFP to higher levels than did YF/Cfrs/GFP. Taken together, the results of these experiments and those presented in the previous section, indicated that YFV capsid expressed outside of its natural context has a strong effect on the cytopathogenicity of the recombinant viruses and consequently on their growth in tissue culture. In the additional experiments, the cytotoxicity of the constructs was shown not to depend on the capsid expression in the GFP-fused or free form (data not shown). The only noticeable effect between the GFP expressed in a fused or free form was in its intracellular distribution.

EXAMPLE 11

Selection of YFV Variants with Reduced Cytopathogenicity

In the described above experiments, the YF/C/GFP/C virus, containing two copies of capsid gene, demonstrated a highly unusual replication (FIG. 2B), characterized by very inefficient release of infectious virus within first three days post transfection of the in vitro-synthesized RNA and death of the majority of cell population. However, a small percentage of the GFP-positive cells survived, continued to grow and after 72 h post transfection, produced virus more efficiently than during the early times post transfection (FIG. 2B). By day 5, virus titers approached 108 inf.u/ml. These data suggested a possibility of accumulation of the mutations in the viral genomes that could affect its highly cytopathic phenotype and lead to prolonged, more efficient infectious virus release.

Figures 3A, 3B:
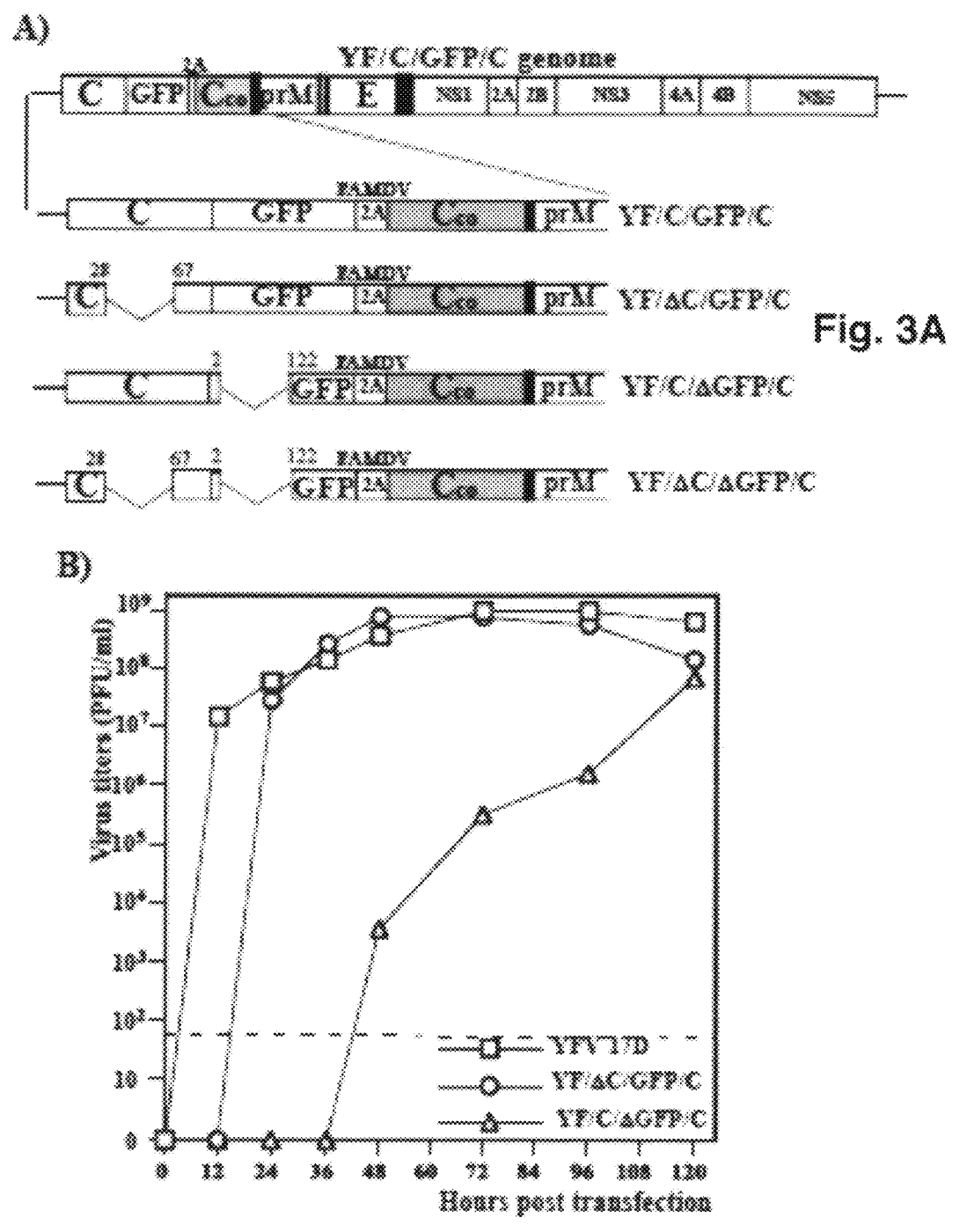

To identify these adaptive changes, the 5'UTR, the amino terminal capsid- and GFP-encoding fragment of the randomly selected mutants were sequenced. They contained large in frame deletions in both capsid (a.a. 29-66) or GFP (a.a. 3-121) genes, or both deletions together (FIG. 3A). Interestingly, the deletions occurred between very short (UAAA; SEQ ID NO: 1) repeats, located in capsid sequence (in the loops of the computer-predicted secondary structure), and UGGUGA (SEQ ID NO: 2) repeats in the GFP gene. These sequencing data were insufficient for conclusive understanding which deletion had critical positive effect on virus replication. Therefore, both GFP- and capsid-specific deletions were separately cloned into YF/C/GFP/C genome (FIG. 3B). The in vitro-synthesized RNAs were transfected into BHK-21 cells, and only the deletion in capsid demonstrated a positive effect on the yield of infectious virus release. The recombinant YF/DC/GFP/C, but not the YF/C/DGFP/C, demonstrated growth rates similar to those of YFV 17D (FIG. 3B). Thus, the results of these experiments suggested that modifications of the first capsid-coding sequence might be a very efficient means of altering replication efficiency of the virus and construction of the variants capable of efficient propagation in tissue culture.

EXAMPLE 12

Development of the YFV Capable of Expressing Heterologous Genes

To experimentally test the possibility of designing YFV capable of efficient replication and stable expression of the heterologous genes, two recombinant YFV genomes, YF/GFP and YFmut/GFP were designed. A 75 nt-long fragment of the capsid-coding sequence was cloned upstream of the GFP and FAMDV 2A genes, which were followed by the entire YFV polyprotein-coding sequence (FIG. 4A), containing a codon-optimized capsid gene. YF/GFP had no any other changes in the 5'-terminal sequence, and, in the YFmut/GFP, the additional modifications were as follows: i) the UGGUGA (SEQ ID NO: 2) sequence in GFP was replaced by UCGUCA (SEQ ID NO: 3) that did not change the encoded protein sequence, but modified one of the repeats that were found to be used during the deletion formation in the YF/C/DGFP and YF/DC/DGFP genomes; ii) a short fragment between the cyclization sequence and GFP was modified by making three single-nucleotide insertions.

The GFP-specific mutations were made to additionally decrease the possibility of recombination in the GFP gene leading to deletions of the coding sequence. The changes in the capsid-coding sequence were made to avoid possible recombination between the residual, 75-nt-long sequence in the beginning of the ORF with the codon-optimized capsid gene, located downstream of the GFP. The in vitro-synthesized RNAs were transfected into BHK-21 cells. Essentially all of the cells demonstrated very similar levels of GFP expression that was detectable within 18 h post transfection, thereby suggesting that both viruses were viable and did nor require additional adaptation for replication. The YF/GFP and YFmut/GFP viruses were less cytopathic than wt YFV 17D, and GFP-positive cells continued to grow until reaching a complete confluency. However, in spite of the reduced cytopathogenicity, both viruses were capable of efficient replication and accumulated in the medium to the titers higher than $5 \times 10^8$ inf.u/ml (FIG. 4B).

To evaluate the stability of the GFP insertion, one of the stocks of YFmut/GFP virus was blindly passaged 5 times in BHK-21 cells. No significant change were detected in titer of the harvested samples (FIG. 4C). After 5 passages, 11% of foci were GFP-negative, but were stained by YFV-specific antibodies. These GFP variants were still incapable of developing plaques, thereby suggesting that the mutations likely accumulated in the GFP gene due to lack of positive selection for functional protein, but not as a result of selection of better replicating virus. The PCR-based analysis also did not detect fragments that were noticeably shorter than expected. Thus, if cassettes expressing the heterologous genes other than GFP were used, no difference in the protein production would be detected.

In another experiment, 6-day-old mice with $5 \times 10^6$ and $5 \times 10^5$ inf.u of YF/GFP were intra cranially inoculated. All of the mice developed clinical signs of encephalitis and were euthanized at day 8 post infection. All of the mice demonstrated presence of the GFP-expressing virus in the brain at a concentration $2.46 \pm 0.68 \times 10^8$ inf.u/ml. No better replicating variants, expressing higher level of GFP or demonstrating more cytopathic phenotype, were detected. Eight days post infection, virus samples, isolated from the brain, also contained less than 3% of GFP-negative variants. These data suggested that the designed strategy of the YFV genome modification aimed at separating the functional polyprotein-coding sequence and the promoter elements opens an opportunity for stable expression of heterologous proteins. YF/GFP and YFmut/GFP demonstrate very similar characteristics of the replication, nevertheless, the YFmut-based vectors are probably more preferential for the studies that require long-term experiments and/or repeating passaging.

EXAMPLE 13

Trans-Complementation Between Two Defective YFV Genomes

Figures 5A, 5B, 5C, 5D, 5E, 5F:
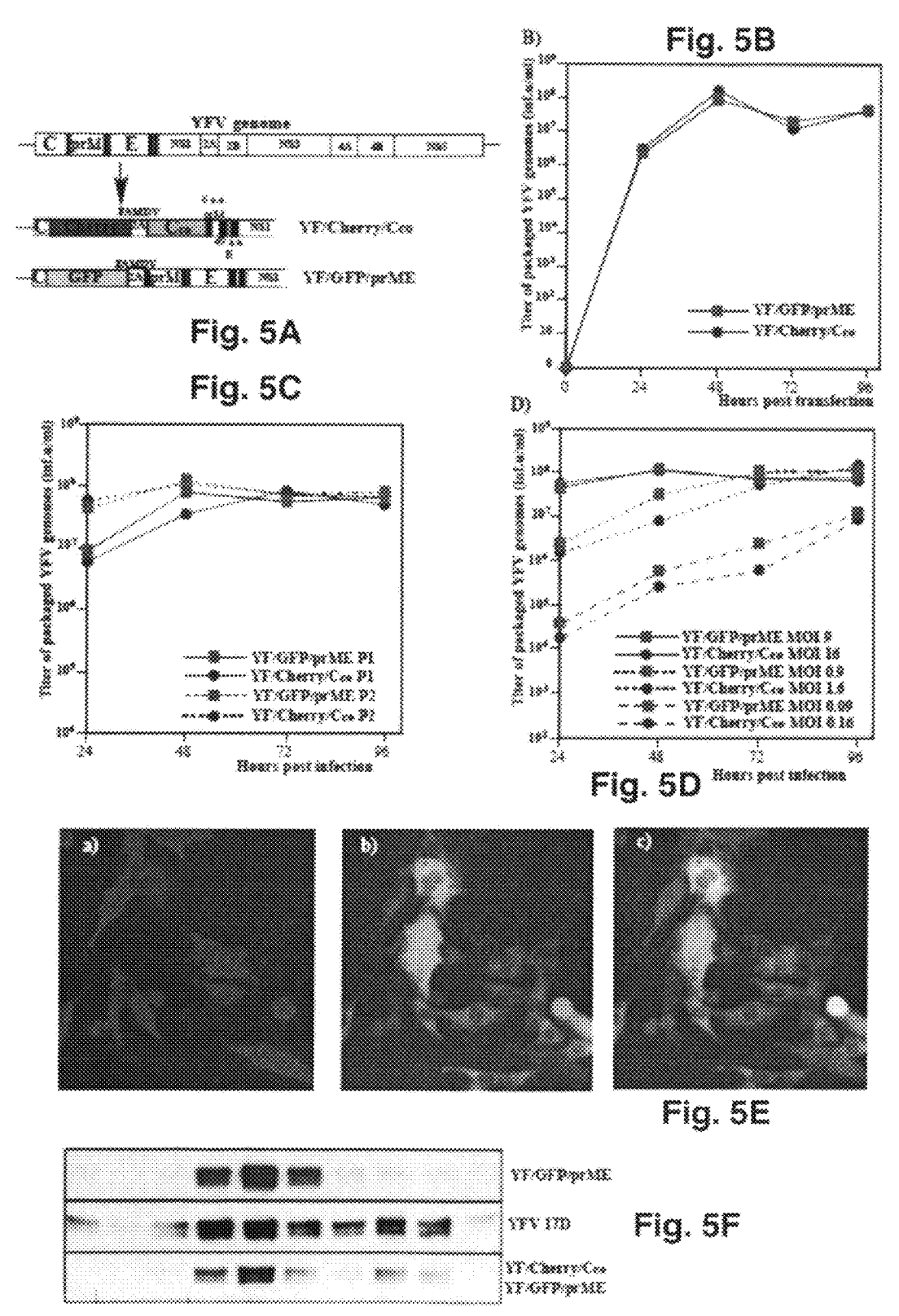

Based on the data of the above-described experiments, a defective in replication YFV genome, YF/Cherry/Cco was designed (FIG. 5A). This was capable of expression of the capsid gene and had a deleted the prM/E-coding sequence. It contained a YFV 5'UTR, followed by 25 a.a. of capsid, Cherry, FAMDV 2A, Cco with prM-specific signal peptide and the carboxy terminal fragment of E protein required for proper processing and compartmentalization of the following NS1-5 polyprotein. The in vitro-synthesized YF/Cherry/Cco and the trans-complementing counterpart, YF/GFP/prME genomes were transfected into BHK-21 cells. They complemented the each other's deficiencies in the structural protein synthesis, and the cells efficiently produced infectious viral particles having either capsid- or prM/E-encoding, defective genomes capable of expression Cherry or GFP, respectively (FIG. 5B). Importantly, both genomes were packaged to very similar titers approaching 108 inf.u/ml. They caused CPE inefficiently and readily established a persistent infection. Cells continued to grow and produced viruses not only 4-5 days post transfection, but also after their passaging.

To test a possibility of large-scale production, virus stocks were further passaged in naïve BHK-21 cells, and titers of particles containing each genome approached 108 inf.u/ml. Moreover, it was not necessary to perform passaging at a high MOI. Cells infected at an MOI of ~1 inf.u/cell released packaged genomes as efficiently as those infected at an MOI of ~10 inf.u/cell. However an additional decrease in MOI to ~0.1 inf.u/cell made virus titers noticeably lower (FIG. 5D). In the cell monolayers infected at an MOI of 1, the cells expressing only one GFP or Cherry marker could be readily detected. However, a very large fraction of them expressed both (FIG. 5E). Analysis of virus density in the sucrose gradients demonstrated that cells transfected with YF/GFP/prME RNA released only low-density viral particles, corresponding to prM/E containing so-called subviral particles (SVPs) lacking the nucleocapsid and RNA. However, infection with viruses containing both defective trans-complementing genomes led to release of both low and high-density particles demonstrating in sucrose density gradient the same distribution as did the samples of the wt YF 17D virus. These data additionally indicated that virus with two-component genome demonstrates the characteristics similar to those of the natural YFV.

EXAMPLE 14

Packaging of the YFV Replicons Lacking the Structural Genes

In a previous study, a cell line expressing YFV C-prM-E cassette was developed from a persistently replicating VEEV replicon. This cell line efficiently functioned in packaging YF/prME/GFP defective virus genome, and this activity indicated that capsid protein was produced and properly processed for genome encapsidation. However, the same cell line was inefficient in packaging YF replicons encoding no structural proteins. As a result, titers of packaged replicons were always below $10^7$ inf.u/ml. The reason for this low level of packaging was not clear, but these data correlated with the previously published results of another study, in which Sindbis virus replicons producing YF C-prM-E cassette packaged similar YF replicons inefficiently as well.

To test possibility of packaging YF replicons to higher titers, we designed VEEV replicons encoding YFV C-prM-E in the same fusion protein as in YF/GFP/Cco viral genome. One of the subgenomic RNAs encoded ORF that started with 25 a.a. of capsid protein, continued into GFP gene, FAMDV 2A protease, codon-optimized capsid and prM/E coding sequence. The second subgenomic RNA was driving the expression of PAC gene, encoding puromycin acetyltransferase that makes cells resistant to translational arrest caused by the presence of puromycin in the medium. The in vitro-synthesized VEErep/GFP-C-prM-E/Pac RNA was transfected into BHK-21 cells and Pur cell line was established within few days of Pur selection. Then cells were transfected with YFV replicon (YFrep/Cherry), in which all of the structural genes were replaced by Cherry-coding sequence (FIG. 6A). As indicated in FIG. 6B, the cell line packaged the latter replicon to greatly higher titers, and continued to produce the infectious particles within a few days without development of profound CPE (FIG. 6C). The YF replicon-containing cells continued to grow, and usually the experiments were terminated, because the cells, expressing both GFP and Cherry, reached confluency that caused their death. In multiple experiments, no packaging of VEEV replicons into YFV structural proteins was ever detected. An additional advantage of the VEErep/GFP-C-prM-E/Pac-containing cell line was in possibility of using it for further passaging of YFV replicons. These cells could be infected with the previously packaged constructs, and this led to development of spreading infection and release of replicon-containing particles to the titers approaching $10^8$ inf.u/ml.

The following references were cited herein:
Aberle et al. (1999). *J Immunol* 163(12), 6756-61.
Aberle et al. (2005). *J Virol* 79(24), 15107-13.
Chambers et al. (1999) *J Virol* 73(4), 3095-101.
Colombage et al. (1998) *Virology* 250(1), 151-63.
Davis et al. (2001) *Journal of Virology* 75(9), 4040-4047.
Kochel et al. (1997) *Vaccine* 15(5), 547-52.
Kochel et al (2000). *Vaccine* 18(27), 3166-3173.
Kofler et al (2004) *Proc Natl Acad Sci USA* 101(7), 1951-6.
Konishi and Fujii (2002) *Vaccine* 20(7-8), 1058-67.
Konishi et al (2001) *Journal of Virology* 75(5), 2204-2212.
Konishi, et al (1992) *Virology* 188(2), 71420.
Konishi, et al (2000a) *Vaccine Jan.* 18(11-12), 1133-1139.
Konishi, et al. (2000b) *Virology* 268(1), 49-55.
Lindenbach and Rice (2001). *Flaviviridae*: The Viruses and Their Replication. Fourth ed. In "Fields Virology" (D. M. Knipe, P. M. Howley, D. G. Griffin, R. A. Lamb, M. A. Martin, and B. Roizman, Eds.), Vol. 1, pp. 991-1041.2 vols. Lippincott Williams & Wilkins, Philadelphia.
Lorenz et al (2002) *J Virol* 76(11), 5480-91.
Mason et al (1991) *Virology* 180(1), 294-305.
Mason et al (2006) *Virology* 351(2), 432-43.
Monath, et al (2002) *Vaccine* 20(7-8), 1004-18.
Phillpotts et al (1996) *Arch Virol* 141(3-4), 743-9.
Qiao et al (2004) *J Infect Dis* 190(12), 2104-8.
Schmaljohn et al (1997) *J Virol* 71(12), 9563-9.

---

What is claimed is:

1. A two-component genome flavivirus composition, comprising:
a first virus particle comprising a first viral genome encoding (i) an amino-terminal capsid fragment having more than the first 20 and at most the first 25 amino acids of the capsid protein, wherein the capsid fragment is not capable of nucleocapsid formation, (ii) a 5' UTR, (iii) cis-acting promoter elements required for RNA replication, (iv) envelope proteins, and (v) a complete set of non-structural proteins of the flavivirus; and
a second virus particle comprising a complementing second viral genome encoding (i) a 5' UTR, (ii) cis-acting promoter elements required for RNA replication, (iii) capsid protein, and (iv) a complete set of non-structural proteins of the flavivirus.

2. The composition of claim 1, wherein said first virus particle or said second virus particle comprises a ubiquitine or a foot-and-mouth disease (FAMDV)-specific 2A protease fused to the sequence encoding the envelope proteins or the capsid protein.

3. The composition of claim 1, wherein the first viral genome or the complementing second genome, or both further comprise a heterologous nucleic acid.

4. The composition of claim 1, wherein the flavivirus is yellow fever virus, West Nile virus, dengue virus, tick-borne encephalitis virus, Saint Louis encephalitis virus, Japanese encephalitis virus, Murray Valley encephalitis virus, classical swine fever virus or hepatitis C virus.

5. A cell culture system comprising a cell infected with the composition of claim 1.

6. The cell culture system of claim 5, wherein the cell is Vero, BHK-21, C7/10 or other cells of vertebrate or mosquito origin.

7. A method of large-scale propagation of two-component genome flavivirus composition, comprising:
infecting a cell in culture with the composition of claim 1 wherein, both genomes replicate in the same cell; and
isolating viral particles produced by the infected cell.

8. The method of claim 7, wherein said cell is infected with the two-component genome flavivirus at a multiplicity of infection of more than 1 infectious unit/cell.

9. The composition of claim 1, further comprising an adjuvant, a pharmaceutically acceptable carrier or combinations thereof.

10. A method of inducing an immune response in a subject comprising:
administering the composition of claim 1 to the subject.

11. The method of claim 10, wherein said administration is via intraperitoneal, intradermal, subcutaneous, intramuscular, oral or intranasal route.

12. The method of claim 10, wherein said flavivirus is yellow fever virus, West Nile virus, dengue virus, tick-borne encephalitis virus, Saint Louis encephalitis virus, Japanese encephalitis virus, Murray Valley encephalitis virus, classical swine fever virus or hepatitis C virus.

13. The composition of claim 1, wherein the amino terminal fragment of capsid protein is the first 25 amino acids of the capsid protein.

14. A two-component genome flavivirus composition, comprising:
a first flavivirus genome encoding (i) an amino-terminal capsid fragment having more than the first 20 and at most the first 25 amino acids of the capsid protein, wherein the capsid fragment is not capable of nucleocapsid formation, and (ii) an envelope protein; and
a second flavivirus genome (i) encoding a capsid protein capable of forming a nucleocapsid and (ii) having a deletion of the envelope genes.

* * * * *

SEQUENCE LISTING

```
<160> NUMBER OF SEQ ID NOS: 14

<210> SEQ ID NO 1
<211> LENGTH: 4
<212> TYPE: RNA
<213> ORGANISM: artificial sequence
<220> FEATURE:
<223> OTHER INFORMATION: Repeat in the Yellow Fever virus capsid
      sequence

<400> SEQUENCE: 1 uaaa                                                                   4

<210> SEQ ID NO 2
<211> LENGTH: 6
```

```
<212> TYPE: RNA
<213> ORGANISM: artificial sequence
<220> FEATURE:
<223> OTHER INFORMATION: Repeat in the green fluorescent protein (GFP)
      gene from Aequorea victoria

<400> SEQUENCE: 2 ugguga                                                                     6

<210> SEQ ID NO 3
<211> LENGTH: 6
<212> TYPE: RNA
<213> ORGANISM: artificial sequence
<220> FEATURE:
<223> OTHER INFORMATION: Modification in the green fluourescent protein
      gene repeat in the recombinant yellow fever/green fluorescent
      protein gene YFmut/GFP plasmid

<400> SEQUENCE: 3 ucguca                                                                     6

<210> SEQ ID NO 4
<211> LENGTH: 6
<212> TYPE: PRT
<213> ORGANISM: artificial sequence
<220> FEATURE:
<223> OTHER INFORMATION: Yellow fever virus capsid protein sequence in
      YF/C/Cherry plasmid

<400> SEQUENCE: 4

Leu Leu Met Thr Gly Gly
              5

<210> SEQ ID NO 5
<211> LENGTH: 6
<212> TYPE: PRT
<213> ORGANISM: artificial sequence
<220> FEATURE:
<223> OTHER INFORMATION: Yellow fever virus prM protein sequence in
      YF/C/Cherry plasmid

<400> SEQUENCE: 5

Val Thr Leu Val Arg Lys
              5

<210> SEQ ID NO 6
<211> LENGTH: 5
<212> TYPE: PRT
<213> ORGANISM: artificial sequence
<220> FEATURE:
<223> OTHER INFORMATION: Fluorescent Cherry protein sequence in
      YF/C/Cherry plasmid

<400> SEQUENCE: 6

Glu Leu Tyr Lys Asp
              5

<210> SEQ ID NO 7
<211> LENGTH: 6
<212> TYPE: PRT
<213> ORGANISM: artificial sequence
<220> FEATURE:
<223> OTHER INFORMATION: Yellow fever virus envelope protein sequence in
      YF/C/Cherry plasmid

<400> SEQUENCE: 7

Leu Phe Gly Gly Leu Asn
              5
```

-continued

<210> SEQ ID NO 8
<211> LENGTH: 5
<212> TYPE: PRT
<213> ORGANISM: artificial sequence
<220> FEATURE:
<223> OTHER INFORMATION: Yellow fever virus capsid protein sequence in
      YF/GFP/prME plasmid

<400> SEQUENCE: 8

Arg Ser Leu Ser Asn
                5

<210> SEQ ID NO 9
<211> LENGTH: 6
<212> TYPE: PRT
<213> ORGANISM: artificial sequence
<220> FEATURE:
<223> OTHER INFORMATION: GFP sequence in YF/GFP/prME plasmid

<400> SEQUENCE: 9

Thr Met Val Ser Lys Gly
                5

<210> SEQ ID NO 10
<211> LENGTH: 5
<212> TYPE: PRT
<213> ORGANISM: artificial sequence
<220> FEATURE:
<223> OTHER INFORMATION: GFP in YF/GFP/prME plasmid

<400> SEQUENCE: 10

Glu Leu Tyr Lys Leu
                5

<210> SEQ ID NO 11
<211> LENGTH: 17
<212> TYPE: PRT
<213> ORGANISM: artificial sequence
<220> FEATURE:
<223> OTHER INFORMATION: Foot-and-mouth disease virus FAMDV 2A protein
      in YF/GFP/prME plasmid

<400> SEQUENCE: 11

Asn Phe Asp Leu Leu Lys Leu Ala Gly Asp Val Glu Ser Asn Pro
                5                   10                  15

Gly Pro

<210> SEQ ID NO 12
<211> LENGTH: 5
<212> TYPE: PRT
<213> ORGANISM: artificial sequence
<220> FEATURE:
<223> OTHER INFORMATION: Yellow fever virus capsid protein sequence in
      YF/GFP/prME plasmid

<400> SEQUENCE: 12

Arg Ser His Asp Val
                5

<210> SEQ ID NO 13
<211> LENGTH: 87
<212> TYPE: RNA
<213> ORGANISM: artificial sequence
<220> FEATURE:
<223> OTHER INFORMATION: Yellow fever virus capsid gene sequence in
      YF/GFP plasmid

<400> SEQUENCE: 13

```
augucugguc guaaagcuca gggaaaaacc cugggcguca auaugguacg        50
acgaggaguu cgcuccuugu caaacaccau ggugagc                     87

<210> SEQ ID NO 14
<211> LENGTH: 90
<212> TYPE: RNA
<213> ORGANISM: artificial sequence
<220> FEATURE:
<223> OTHER INFORMATION: Yellow fever virus capsid gene sequence in
      YFmut/GFP plasmid

<400> SEQUENCE: 14
augucugguc guaaagcuca gggaaaaacc cugggcguca auaugguaac        50
gacgaggagu ucgcuccuug ucaaaccacc ggucgucagc                  90
```